United States Patent [19]

Genzer et al.

[11] 3,960,856

[45] June 1, 1976

[54] PROCESS FOR THE PREPARATION OF 4-HYDROXY-3-(5-METHYL-3-ISOXAZOLYLCARBAMOYL)-2-METHYL-2H-1,2-BENZOTHIAZINE 1,1-DIOXIDE

[75] Inventors: Jerome D. Genzer, Livingston; Francisco Carrio Fontsere, Pasippany, both of N.J.

[73] Assignee: Warner-Lambert Company, Morris Plains, N.J.

[22] Filed: June 20, 1975

[21] Appl. No.: 588,752

[52] U.S. Cl............................................ 260/243 R
[51] Int. Cl.² ..................................... C07D 279/02
[58] Field of Search ................................ 260/243 R

[56] References Cited
UNITED STATES PATENTS
3,821,211   6/1974   Sircar et al. ........................ 260/243

*Primary Examiner*—John M. Ford
*Attorney, Agent, or Firm*—Albert H. Graddis; Frank S. Chow; Anne M. Kelly

[57] ABSTRACT

An improved process for the preparation of 4-hydroxy-3-(5-methyl-3-isoxazolylcarbamoyl)-2-methyl-2H-1,2-benzothiazine 1,1-dioxide (I), a known anti-inflammatory agent, requires the use of specific proportions of reactants and carefully controlled reaction conditions. An alkali metal alkoxide, suspended in dimethylformamide is combined, with stirring, as rapidly as possible with a solution of alkyl 2,3-dihydro-3-oxo-1,2-benzisothiazole-2-acetate 1,1-dioxide (II) in dimethylformamide, while maining the internal reaction temperature within 15°–30°C. More than two but less than six moles of the alkoxide are used per mole of the alkyl 2,3-dihydro-3-oxo-1,2-benzisothiazole-2-acetate 1,1-dioxide (II). After all reactants have been combined, stirring is continued for a specific period of time and then the reaction mixture is acidified. Total elapsed time from initial combination of reactants to acidification is from 30 to 50 minutes. Acidification of the reaction mixture precipitates out alkyl 4-hydroxy-2H-1,2-benzothiazine-3-carboxylate 1,1-dioxide (III) in substantially pure form in high yields, without recrystallization. Product III is methylated on the sulfonamide nitrogen and reacted with 3-amino-5-methyl-isoxazole to obtain crude I. A further improvement in the process of the invention involves a more efficient method for purifying crude product I: the need for large quantities of dioxane solvent is obviated. After slurrying and washing, product I is solubilized in dilute alkali, and decolorized. After filtration and acidification pure product I in high yield is obtained. In addition to preparing the known anti-inflammatory agent (I), the initial reaction step of the invention wherein 2,3-dihydro-3-oxo-1,2-benzisothiazole-2-acetate, 1,1-dioxide (II) is rearranged to form alkyl 4-hydroxy-2H-1,2-benzothiazine-3-carboxylate 1,1-dioxide (III), may be used with particular advantage for the preparation of other useful benzothiazine derivatives.

14 Claims, No Drawings

PROCESS FOR THE PREPARATION OF 4-HYDROXY-3-(5-METHYL-3-ISOXAZOLYLCARBAMOYL)-2-METHYL-2H-1,2-BENZOTHIAZINE 1,1-DIOXIDE

BACKGROUND OF THE INVENTION

1. Field of the Invention

The present invention relates to an improved process for the preparation of 4-hydroxy-3-(5-methyl-3-isoxazolylcarbamoyl)-2-methyl-2H-1,2-benzothiazine 1,1-dioxide (I).

2. Description of the Prior Art

The preparation of 4-hydroxy-3-(5-methyl-3-isoxazolylcarbamoyl)-2-methyl-2H-1,2-benzothiazine 1,1-dioxide (I) has been described by Zinnes et al. in U.S. Pat. No. 3,822,258. Other novel routes to its preparation have also been described by Sircar et al. in U.S. Pat. No. 2,821,211 and by Lombardino in U.S. Pat. No. 3,853,862. The following intermediates of interest in the process of this invention:

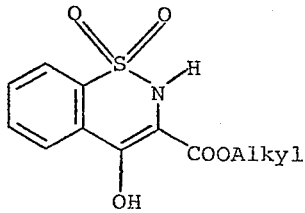

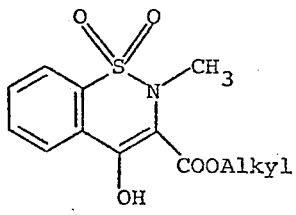

have been disclosed in U.S. Pat. Nos. 3,501,466 and 3,591,584 and by Lombardino et al., J. Med. Chem. 14: 173 (1971). These intermediates were used by Zinnes in U.S. Pat. No. 3,822,258 for the preparation of the subject compound (I) and by Lombardino in U.S. Pat. No. 3,591,584 for the preparation of related benzothiazine amides, useful as anti-inflammatory agents.

DESCRIPTION OF THE PARTICULAR EMBODIMENTS

According to the present invention, an improved process for the production of 4-hydroxy-3-(5-methyl-3-isoxazolylcarbamoyl)-2-methyl-2H-1,2-benzothiazine 1,1-dioxide (I):

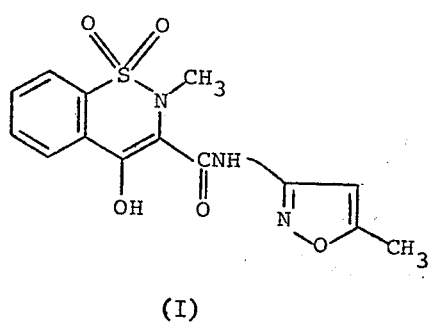

(I)

involves a multi-step procedure wherein, in an improved initial reaction step, a suspension of an alkali metal alkoxide of a lower alcohol in dimethylformamide is combined, with stirring, with a solution of compound II:

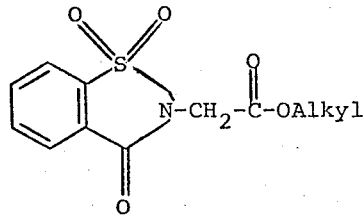

Alkyl 2,3-dihydro-3-oxo-1,2-benzisothiazole-2-acetate 1,1-dioxide (II)

in dimethylformamide, as rapidly as possible while maintaining the internal reaction temperature betwwen 15°to 30°C. Preferably, the solution of II is added to the suspension of the alkali metal alkoxide in dimethylformamide. More than two but less than six moles of the alkoxide are used for each mole of the alkyl 2,3-dihydro-3-oxo-1,2-benzisothiazole-2-acetate 1,1-dioxide (II). The compound II alkyl ester may be a 1 to 7 carbon lower alkyl ester, and in order to achieve optimum yields in this improved initial reaction step, the alkyl group in the alkoxide reagent must correspond to the compound II alkyl ester.

After the combination of reactants has been completed, stirring is continued for a specific period of time. Upon completion of reaction time, the reaction mixture is acidified. The total time from the initial combination of reactants to acidification should be from about 20 to about 60 minutes, preferably from about 30 minutes to about 50 minutes. Acidification of the reaction mixture with a dilute mineral acid precipitates out compound III:

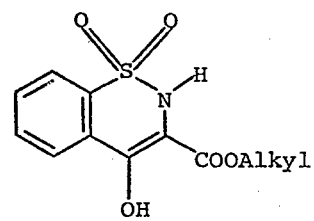

Alkyl 4-hydroxy-2H-1,2-benzothiazine-3-carboxylate 1,1-dioxide (III)

The compound III alkyl ester is a 1 to 7 carbon atom lower alkyl ester, corresponding to the compound II alkyl ester. Compound III is obtained in substantially pure form and in high yield, without the need for recrystallization according to the improved initial reaction process of this invention. Yields in the range of 72 to 82% are obtained and compound III may be used directly in subsequent reaction steps leading to the preparation of compound I.

It should be noted that, in contrast to the statement made in the prior art (J. Med. Chem. 14: 173, 1971), the yield in the above-described reaction, when carried out in the dimethylformamide solvent, is consistently high. Quite surprisingly, it has been found that the improved initial reaction step of this invention may be performed in dimethylformamide in a reproducible manner which is easily adapted to large scale production techniques. Additionally, the yield and purity of compound III prepared according to the improved initial reaction step of this invention is significantly higher than has been previously reported for other reaction conditions. Thus, the reaction conditions described above are critical: higher temperatures, the use of mole ratios outside the stated ranges or the extension of reaction and stirring times have been found to significantly reduce the purity of the product obtained as well as to lower the overall yield of compound III.

As has been stated above, the substantially pure form of compound III obtained according to the improved initial reaction step of this invention is subsequently subjected to additional reactions to obtain the desired compound I. For example, a conventional methylation reaction is conducted at about 25°C. using a suitable methylating agent, such as dimethylsulfate and sodium hydroxide in either an aqueous lower alcohol solution or in dimethylformamide, to obtain compound IV:

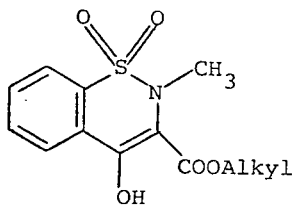

Alkyl 4-hydroxy-2-methyl-
2H-1,2-benzothiazine-3-
carboxylate 1,1-dioxide (IV)

Again, the alkyl group in compound IV may be a 1 to 7 carbon atom lower alkyl group corresponding to the compound III alkyl ester.

The final step in the preparation of compound I is carried out in a manner similar to that described by Zinnes in U.S. Pat. No. 3,822,258, i.e., reaction with 3-amino-5-methylisoxazole in a xylene solvent. However, according to the process of this invention, it has been found that the use of a molecular sieve is unnecessary. Instead, the xylene solution of compound IV and 3-amino-5-methylisoxazole are refluxed for about 13–18 hours. In a preferred refluxing procedure, about 3 to 4% of the xylene solvent is distilled off periodically and replaced with fresh xylene at about four hour intervals. When refluxing has been completed, the reaction mixture is cooled and filtered to obtain crude product I. According to prior art procedures, crude product I must be recrystallized from large amounts of dioxane solvent in order to obtain pure product I. It has now been found, according to an improved final reaction step of this invention, that crude product I can be purified with high recovery (about 90%) without the need for recrystallization from large amounts of dioxane solvent.

According to the improved final reaction step of this invention, a slurry of crude product I in an organic solvent such as dimethylformamide, dimethylsulfoxide, or 1 to 3 carbon lower alcohols, and the like is stirred at room temperature for about 15–45 minutes. Among these solvents, dimethylformamide is preferred. The slurry is filtered and the filter cake obtained is washed with water to remove solvent residue. Next the washed filter cake is suspended in water and a sufficient amount of an alkali or alkaline earth metal hydroxide is added to form a solution. Preferably, dilute sodium hydroxide is used. A charcoal decolorizing agent, such as boneblack, is added to the solution and the solution is heated to below boiling for a time sufficient to achieve decolorization (approximately 5 to 10 minutes). Filtration removes the decolorizing agent. The filtered solution is then acidified with a mineral acid, cooled to room temperature and filtered to obtain substantially pure 4-hydroxy-3-(5-methyl-3-isoxazolylcarbamoyl)-2-methyl-2H-1,2-benzothiazine 1,1-dioxide (I) in high yield.

The above purification procedure eliminates the need for large volumes of costly, hazardous dioxane solvent which was required in the prior art recrystallization purification process. Thus, the improved multi-step process of this invention for preparing 3-(5-methyl-3-isoxazolylcarbamoyl)-2-methyl-2H-1,2-benzothiazine 1,1-dioxide (I), a useful anti-inflammatory agent, provides a substantial advantage over previouly described methods and permits large scale production of this product much more economically.

An additional feature of this invention resides in the fact that the improved initial reaction step, wherein alkyl 2,3-dihydro-3-oxo-1,2-benzisothiazole-2-acetate 1,1-dioxide (II) is rearranged to form alkyl 4-hydroxy-2H-1,2-benzothiazine-3-carboxylate 1,1-dioxide (III) may be used with particular advantage for the preparation of known benzothiazine amides and related derivatives, which are useful anti-inflammatory agents.

In order to further illustrate this invention, the following examples are provided:

EXAMPLE 1

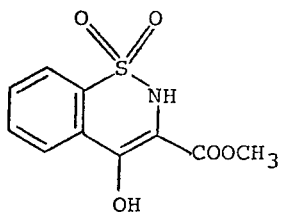

Preparation of Methyl
4-Hydroxy-2H-1,2-Benzothiazine-3-Carboxylate
1,1-Dioxide

In a nitrogen atmosphere, a solution of 30 grams (0.117 moles) of methyl-2,3-dihydro-3-oxo-1,2-benzisothiazoline-2-acetate 1,1-dioxide in 50 ml DMF is added, with stirring, to a suspension of 18.9 grams (0.351 moles) of sodium methoxide in 100 ml DMF over a period of about 5 minutes and the internal temperature is maintained at 15°–30°C. by means of an ice bath. The stirring acidification continued for 30 minutes at about 30°C. after the completion of the addition. With external cooling, a solution of 35 ml concentrated HCl in 600 ml of water is added, maintaining the internal temperature below 35°C. After this addition, the mixture is cooled to 10°C. and filtered. The filter cake is washed thoroughly with water and the product is dried. Yield is 23.5 grams (78.2%) m.p. 173°–175°C. The total addition and stirring time prior to acidification should be less than 1 hour. For example, if the addition should take 30 minutes the batch should be stirred only an additional 15–20 minutes.

EXAMPLE 2

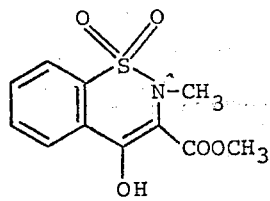

Preparation of Methyl 4-Hydroxy-2-Methyl-2H-1,2-Benzothiazine-3-Carboxylate 1,1-Dioxide To a suspension of 3.5 grams (0.086 moles) of sodium hydroxide in 68 ml DMF, a solution of 20 grams (.078 moles) of methyl 4-hydroxy-2H-1,2-benzothiazine-3-carboxylate 1,1-dioxide is added in 34 ml DMF over a period of about 5 minutes at about 25°C. 11.9 Grams (0.094 moles) of dimethyl sulphate is added over a period of about 30 minutes at a maximum temperature of 30°C. The reaction is stirred for 3 hours at 30°C. and diluted with about 150 ml of water. It is cooled to 15°C., filtered and washed well with water. After drying, there is obtained 20 grams (95%) of product, m.p. 163°–165°C.

EXAMPLE 3

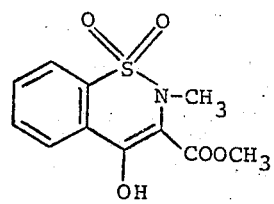

Methyl 4-Hydroxy-2-Methyl-2H-1,2-Benzothiazine-3-Carboxylate-1,1-Dioxide

To a suspension of 90 grams (0.352 moles) of methyl 4-hydroxy-2H-1,2-benzothiazine-3-carboxylate 1,1-dioxide in 450 ml proprietory alcohol there is added a solution of 15.5 grams (0.3875 moles) of sodium hydroxide in 450 ml of water at a temperature of less than 20°C. 53.4 Grams (0.423 moles) of dimethyl sulphate is added while stirring, at 25°C. and the mixture is then allowed to stir for about 15 hours. It is cooled to 10°C. and filtered. The cake is washed with water, followed by a 50% alcohol/water wash, and dried. Yield is 90 grams (95%) m.p. 162.5°–164°C.

EXAMPLE 4

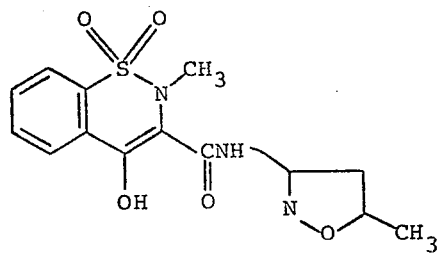

4-Hydroxy-3-(5-Methyl-3-Isoxazolylcarbamoyl)-2-Methyl-2H-1,2-Benzothiazine 1,1-Dioxide To an appropriate flask equipped for reflux and/or distillation, 900 ml xylene, 40 grams (0.149 moles) methyl 4-hydroxy-2-methyl-2H-1,2-benzothiazine-3-carboxylate 1,1-dioxide and 19.94 grams (0.203 moles) of 3-amino-5-methylisoxazole are added. The mixture is refluxed for 13–18 hours. At 1 hour intervals, about 3–4% of the solvent volume is distilled off. Every 4 to 5 hours fresh xylene is added, equal in amount to that distilled during this period. At the end of the heating period, the reaction is cooled to 25°C., filtered and the cake is washed with xylene. After drying, the crude product weighed 43.8 grams (88%). This material could be recrystallized from about 40–50 volumes of dioxane with an 80–85% recovery of acceptable material. An alternate procedure for the purification of crude product is as follows:

EXAMPLE 5

Purification of Crude 4-Hydroxy-3-(5-Methyl-3-Isoxazolylcarbamoyl)-2-Methyl-2H-1,2-Benzothiazine 1,1-Dioxide The crude product is re-slurried in 2 volumes of DMF at 25°C. for 30 minutes. It is filtered and washed well with water. The wet cake is suspended in about 10 volumes of water and solution effected by addition of a slight molar excess of 1 N sodium hydroxide. 10% By weight of Darco is added and the reaction is heated at 90°C. for 30 minutes. The charcoal is filtered and the filtrate is acidified with dilute HCl at about 60°C. to pH=1. The reaction is cooled to less than 20°C. The mixture is filtered and the filter cake obtained is washed well with water and dried. The recovery of purified product is 90%. Analytically, this material is identical with the substance prepared by Zinnes et al. in Example 1 of U.S. Pat. No. 3,822,258.

We claim:
1. An improved process for preparing 4-hydroxy-3-(5-methyl-3-isoxazolylcarbamoyl)-2-methyl-2H-1,2-benzothiazine 1,1-dioxide (I) which comprises the following steps:
   A. suspending more than two but less than six moles of an alkali metal alkoxide of a lower alcohol in dimethylformamide;
   B. dissolving one mole of alkyl 2,3-dihydro-3-oxo-1,2-benzisothiazole-2-acetate 1,1-dioxide (II) in dimethylformamide;
   C. combining the suspension of (A) and the solution of (B) rapidly, with stirring, while maintaining the internal reaction temperature at from about 15° to about 30°C.;
   D. continuing the stirring of the reaction mixture of (C) and then acidifying, with the total time from initial reactant combination to acidification being from about 20 minutes to about 60 minutes;
   E. precipitating from (D) substantially pure alkyl 4-hydroxy-2H-1,2-benzothiazine-3-carboxylate 1,1-dioxide (III) in high yield without recrystallization;
   F. methylating the precipitate of (E) on the sulfonamide nitrogen;
   G. refluxing the alkyl 4-hydroxy-2-methyl-2H-1,2-benzothiazine-3-carboxylate 1,1-dioxide (IV) obtained in (F) with 3-amino-5-methylisoxazole in an inert solvent to obtain crude 4-hydroxy-3-(5-meth- yl-3-isoxazolylcarbamoyl)-2-methyl-2H-1,2-benzothiazine 1,1-dioxide (I);
H. forming a slurry of crude compound I in an organic solvent;
I. stirring the slurry at room temperature for at least 15 minutes;
J. filtering the slurry of (I) and washing the filter cake obtained with water to remove the solvent;
K. suspending the solid cake of (J) in an excess of water and adding a sufficient amount of dilute alkali metal or alkaline earth metal hydroxide to form a solution;
L. adding a charcoal decolorizing agent to (K) and heating to below the boiling point of the solution for a sufficient time to achieve decolorization;
M. filtering the heated solution of (L) to remove the charcoal decolorizing agent; and
N. acidifying the decolorized solution of (M) with a mineral acid, cooling to room temperature, and filtering out substantially pure 4-hydroxy-3-(5-methyl-3-isoxazolylcarbamoyl)-2-methyl-2H-1,2-benzothiazine 1,1-dioxide (I) in high yield.

2. A process according to claim 1 wherein, in Step A, about 3 moles of sodium methoxide are used; and in Step B, about one mole of methyl 2,3-dihydro-3-oxo-1,2-benzisothiazole-2-acetate 1,1-dioxide is used.

3. A process according to claim 1 wherein, in Step D, the total reaction time prior to acidification is from about 30 minutes to about 50 minutes.

4. A process according to claim 1 wherein, in Step G, the inert solvent is xylene.

5. A process according to claim 1 wherein, in Step H, the organic solvent is dimethylformamide.

6. A process according to claim 1 wherein, in Step K, a dilute alkali metal hydroxide is used.

7. A process according to Claim 6 wherein dilute sodium hydroxide is used.

8. A process according to claim 1 wherein, in Step L, a boneblack decolorizing agent is used.

9. A process according to claim 1 wherein, in Step N, hydrochloric acid is used.

10. An improved process for preparing 4-hydroxy-3-(5-methyl-3-isoxazolylcarbamoyl)-2-methyl-2H-1,2-benzothiazine 1,1-dioxide (I) which comprises the following steps:
A. suspending about three moles of sodium methoxide in dimethylformamide;
B. dissolving one mole of methyl 2,3-dihydro-3-oxo-1,2-benzisothiazole-2-acetate 1,1-dioxide in dimethylformamide;
C. combining the suspension of (A) and the solution of (B) rapidly, with stirring, while maintaining the internal reaction temperature at from about 15° to about 30°C.;
D. continuing the stirring of the reaction mixture of (C) and then acidifying, with the total time from initial reactant combination to acidification being from about 30 minutes to about 50 minutes;
E. acidifying the reaction mixture of (D) to precipitate out substantially pure methyl 4-hydroxy-2H-1,2-benzothiazine-3-carboxylate 1,1-dioxide in high yield without recrystallization;
F. methylating the precipitate of (E) on the sulfonamide nitrogen to obtain methyl 4-hydroxy-2-methyl-2H-1,2-benzothiazine-3-carboxylate 1,1-dioxide;
G. refluxing the product of (F) with 3-amino-5-methylisoxazole in xylene to obtain crude 4-hydroxy-3-(5-methyl-3-isoxazolylcarbamoyl)-2-methyl-2H-1,2-benzothiazine 1,1-dioxide (I);
H. forming a slurry of crude compound I in dimethylformamide;
I. stirring the slurry at room temperature for at least 15 minutes;
J. filtering the slurry of (I) and washing the filter cake obtained with water to remove the solvent;
K. suspending the solid cake of (J) in an excess of water and adding a sufficient amount of dilute sodium hydroxide to form a solution;
L. Adding boneblack to (K) and heating to below the boiling point of the solution for a sufficient time to achieve decolorization;
M. filtering the heated solution of (L) to remove the boneblack; and
N. acidifying the decolorized solution of (M) with hydrochloric acid, cooling to room temperature, and filtering out substantially pure 4-hydroxy-3-(5-methyl-3-isoxazolylcarbamoyl)-2-methyl-2H-1,2-benzothiazine 1,1-dioxide (I) in high yield.

11. In a process for preparing alkyl 4-hydroxy-2H-1,2-benzothiazine-3-carboxylate 1,1-dioxide by reacting alkyl 2,3-dihydro-3-oxo-1,2-benzisothiazole-2-acetate 1,1-dioxide with an alkali metal alkoxide in a polar organic solvent, the improvement which comprises:
A. suspending more that two but less that six moles of an alkali metal alkoxide of a lower alcohol in dimethylformamide;
B. dissolving one mole of alkyl 2,3-dihydro-3-oxo-1,2-benzisothiazole-2-acetate 1,1-dioxide in dimethylformamide;
C. combining the suspension of (A) and the solution of (B) rapidly, with stirring, while maintaining the internal reaction temperature between from about 15° to about 30°C.;
D. continuing the stirring of the reaction mixture of (C) and then acidifying, with the total time from initial reactant combination to acidification being from about 20 minutes to about 60 minutes; and
E. precipitating from (D) substantially pure alkyl 4-hydroxy-2H-1,2-benzothiazine-3-carboxylate 1,1-dioxide in high yield without recrystallization.

12. A process according to claim 11 wherein, in Step A, about 3 moles of sodium methoxide are used; and in Step B, about one mole of methyl 2,3-dihydro-3-oxo-1,2-benzisothiazole-2-acetate 1,1-dioxide is used.

13. A process according to claim 11 wherein, in Step C, the solution of (B) is added to the suspension of (A).

14. A process according to claim 11 wherein, in Step D, the total reaction time prior to acidification is from about 30 minutes to about 50 minutes.

* * * * *